(12) United States Patent
Dormer

(10) Patent No.: US 6,436,028 B1
(45) Date of Patent: Aug. 20, 2002

(54) DIRECT DRIVE MOVEMENT OF BODY CONSTITUENT

(75) Inventor: Kenneth J. Dormer, Edmond, OK (US)

(73) Assignee: Soundtec, Inc., Oklahoma City, OK (US)

( * ) Notice: Subject to any disclaimer, the term of this patent is extended or adjusted under 35 U.S.C. 154(b) by 0 days.

(21) Appl. No.: 09/473,017

(22) Filed: Dec. 28, 1999

(51) Int. Cl.[7] .............................................. H04R 25/00
(52) U.S. Cl. ......................................................... 600/25
(58) Field of Search ................... 600/25; 128/897–899; 607/136–137, 55–57; 181/128–137; 381/68–69, 2

(56) References Cited

U.S. PATENT DOCUMENTS

| 2,402,392 A | 6/1946 | Goldschmidt |
| 2,995,633 A | 8/1961 | Puharich et al. |
| 3,209,081 A | 9/1965 | Ducote et al. |
| 3,384,090 A | 5/1968 | Manfredi |
| 3,594,514 A | 7/1971 | Wingrove |
| 3,712,962 A | 1/1973 | Epley |

(List continued on next page.)

FOREIGN PATENT DOCUMENTS

| BE | 833.809 | 3/1976 |
| DE | 1616149 | 1/1968 |
| DE | 2044870 | 9/1970 |
| EP | 0076069 | 4/1983 |
| GB | 553955 | 6/1943 |

OTHER PUBLICATIONS

Daniel Tschumperlin, Melody Swartz, Ning Wang, Roger Kamm, Jeffrey Drazen, and Jeffrey Fredberg, *A Novel Technique for Investigation of Mechanotransduction in Airway Cells*, 1999 Bioengineering Conference, BED–vol. 42, ASME 1999, pp. 521–522.

(List continued on next page.)

*Primary Examiner*—Samuel G. Gilbert
(74) *Attorney, Agent, or Firm*—McAfee & Taft

(57) ABSTRACT

A bio-magnetic system for moving a constituent of a human body includes at least one magnetically responsive member having an attachment mechanism including collagen which is bound with an epithelium of a moveable constituent in the human body. A bio-magnetic drive system for moving a constituent of a human body includes a plurality of magnetic microbeads connected in vivo to a moveable constituent of a human body, and it also includes a magnetic field source disposed in operative association with the microbeads but remote from the microbeads and the moveable constituent to provide a magnetic field to move the microbeads. A method for moving a constituent in a human body includes transmitting a signal to interact with a plurality of microbeads connected to a constituent in a human body such that the connected microbeads and constituent in the human body move in response. A more particular method includes providing a plurality of microbeads in vivo to attach to at least one ossicle in an ear of a human; and processing a sound to drive the microbeads, including transmitting a signal to interact with the microbeads such that the microbeads and the at least one ossicle vibrate in response. Also disclosed are a kit for use in causing a constituent of a human body to move and in vivo methods of connecting microbeads to a constituent in a human body.

34 Claims, 10 Drawing Sheets

U.S. PATENT DOCUMENTS

| | | |
|---|---|---|
| 3,764,748 A | 10/1973 | Branch et al. |
| 3,870,832 A | 3/1975 | Fredrickson |
| 3,882,285 A | 5/1975 | Nunley et al. |
| 3,931,648 A | 1/1976 | Shea, Jr. |
| 4,052,754 A | 10/1977 | Homsy |
| 4,150,262 A | 4/1979 | Ono |
| 4,281,419 A | 8/1981 | Teace |
| 4,284,856 A | 8/1981 | Hochmair et al. |
| 4,292,693 A | 10/1981 | Shea et al. |
| 4,357,497 A | 11/1982 | Hochmair et al. |
| 4,419,995 A | 12/1983 | Hochmair et al. |
| 4,498,461 A | 2/1985 | Hakansson |
| 4,532,930 A | 8/1985 | Crosby et al. |
| 4,606,329 A | 8/1986 | Hough |
| 4,612,915 A | 9/1986 | Hough et al. |
| 4,776,322 A | 10/1988 | Hough et al. |
| 4,800,884 A | 1/1989 | Heide et al. |
| 4,817,607 A | 4/1989 | Tatge |
| RE32,947 E | 6/1989 | Dormer et al. |
| 4,840,178 A | 6/1989 | Heide et al. |
| 4,871,364 A | 10/1989 | Bays et al. |
| 4,918,745 A | 4/1990 | Hutchison |
| 4,921,498 A | 5/1990 | Bays et al. |
| 4,936,305 A | 6/1990 | Ashtiani et al. |
| 5,015,225 A | 5/1991 | Hough et al. ............... 600/25 |
| 5,163,957 A | 11/1992 | Sadé et al. |
| 5,220,918 A | 6/1993 | Heide et al. |
| 5,259,032 A | 11/1993 | Perkins et al. |
| 5,306,299 A | 4/1994 | Applebaum ................ 623/10 |
| 5,338,287 A | 8/1994 | Miller et al. ................ 600/25 |
| 5,344,387 A | 9/1994 | Lupin ......................... 600/25 |
| 5,360,388 A | 11/1994 | Spindel et al. ............. 600/25 |
| 5,425,104 A | 6/1995 | Shennib |
| 5,456,654 A | 10/1995 | Ball ............................ 600/25 |
| 5,486,457 A | 1/1996 | Butler et al. |
| 5,507,303 A | 4/1996 | Kuzma ....................... 128/899 |
| 5,554,096 A | 9/1996 | Ball ............................ 600/25 |
| 5,558,618 A | 9/1996 | Maniglia ................... 600/25 |
| 5,624,376 A | 4/1997 | Ball et al. .................. 600/25 |
| 5,643,783 A | 7/1997 | Olsen et al. |
| 5,655,546 A * | 8/1997 | Halpern ..................... 128/898 |
| 5,741,316 A | 4/1998 | Chen et al. ................ 607/61 |
| 5,776,706 A * | 7/1998 | Siiman et al. ......... 435/7.21 X |
| 5,800,336 A | 9/1998 | Ball et al. .................. 600/25 |
| 5,913,815 A | 6/1999 | Ball et al. .................. 600/25 |
| 6,006,756 A * | 12/1999 | Shadduck .................. 128/899 |
| 6,132,360 A * | 10/2000 | Halpern ..................... 600/9 |

OTHER PUBLICATIONS

Ning Wang, *Integrin–Cytoskeleton Linkages are Important Pathways for Mechanotransduction*, 1999 Bioengineering Conference, BED–vol. 42, ASME 1999, pp. 523–524.

Richard L. Goode, M.D. and Theodore J. Glattke, Ph.D., *Audition via Electromagnetic Induction*, Arch Otolaryngol, vol. 98, pp. 23–26 (Jul. 1973).

Mendell Robinson, M.D. and Stephen D. Kasden, M.S., *Bone Conduction Speech Discrimination, An indication of Cochlear Function in the Immediate Postoperative Period,* Arch Otolaryngol, vol. 103, pp. 238–240 (Apr. 1977).

A. Tjellström, J. Lindström, O. Hallen, T. Albrektsson and P.I. Bronemark, *Direct Bone Anchorage of External Hearing Aids*, J. Biomed. Eng., vol. 5, pp. 59–63 (Jan. 1983).

B. Hakansson, A. Tjellström and U. Rosenhall, *Hearing Thresholds with Direct Bone Conduction Versus Conventional Bone Conduction,* Scand Audiol 13 (11 pages) (Mar. 1984).

* cited by examiner

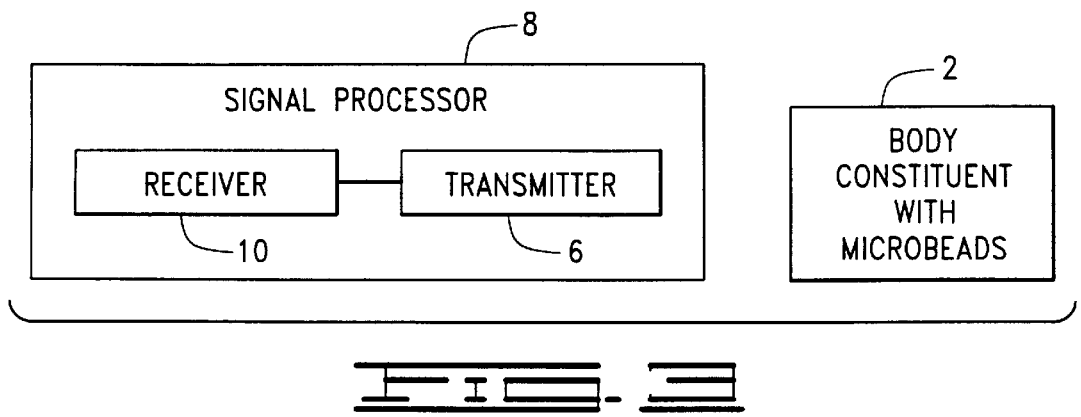
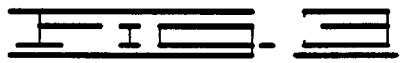
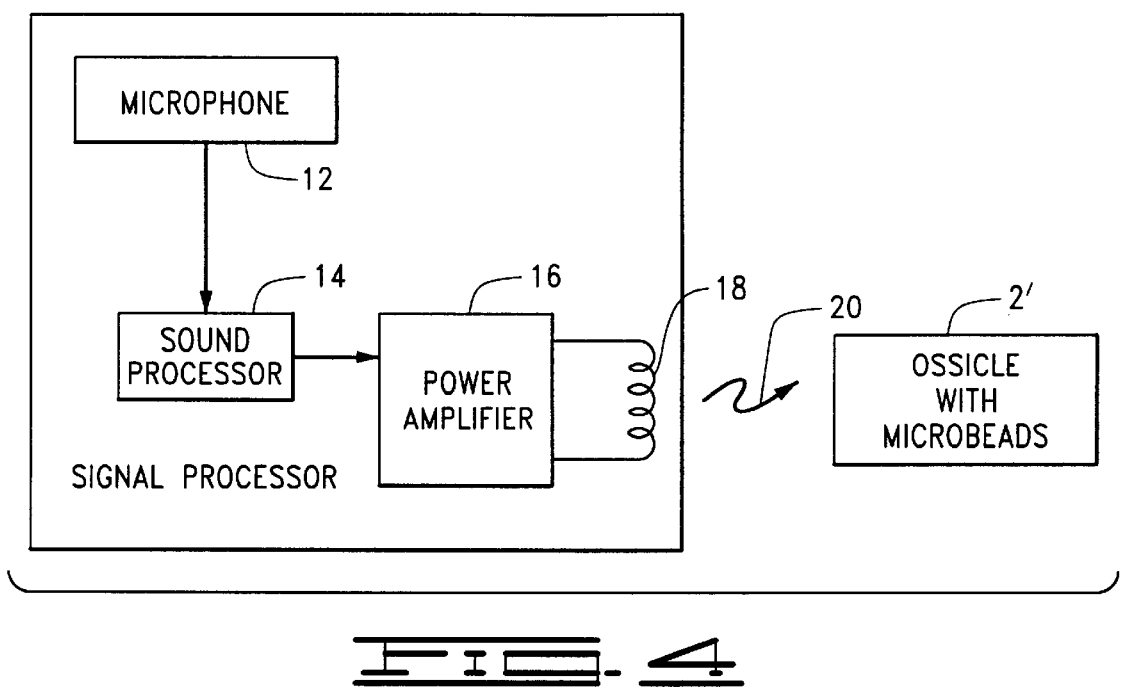

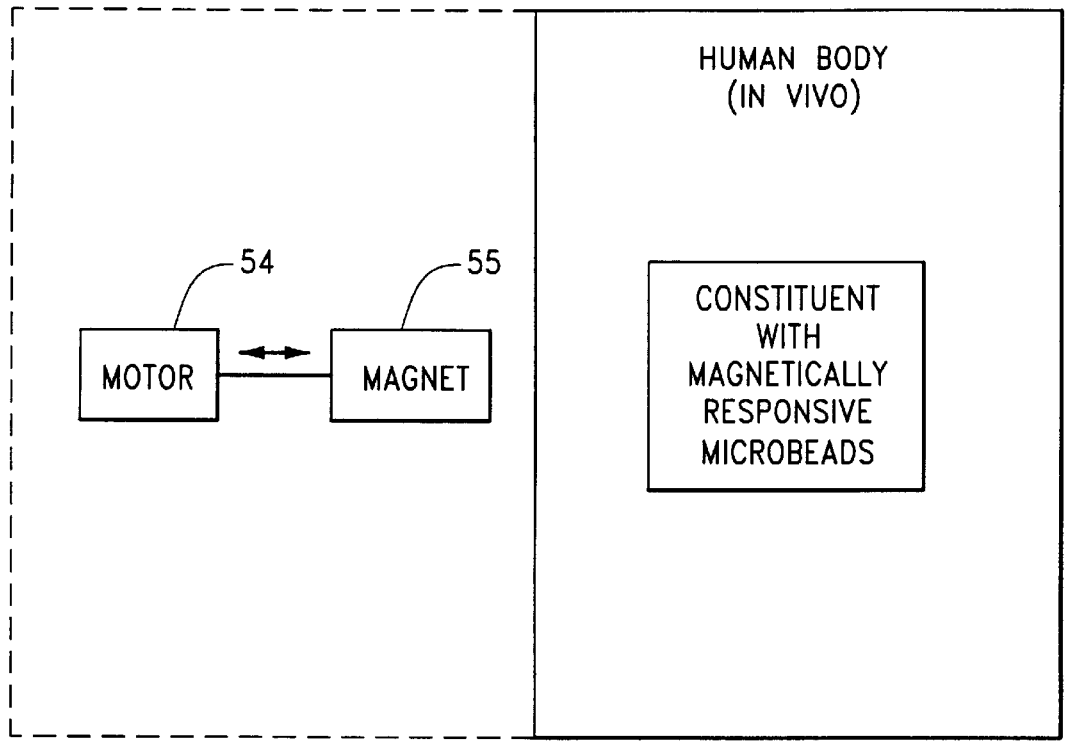
FIG. 10
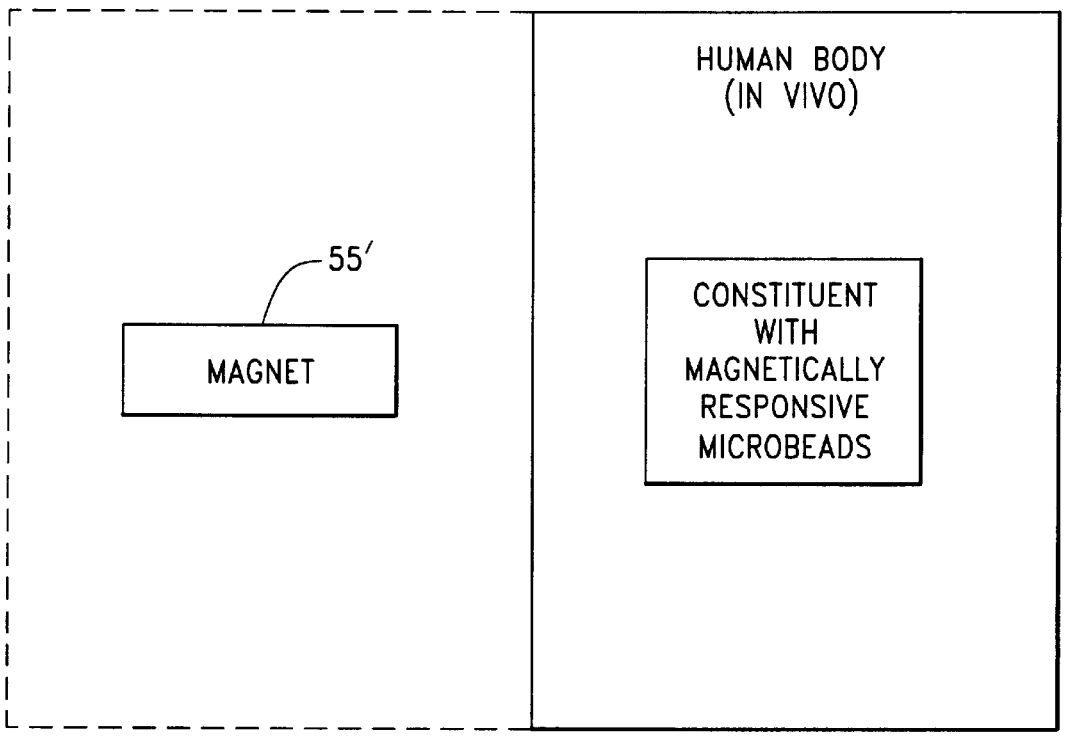
FIG. 11

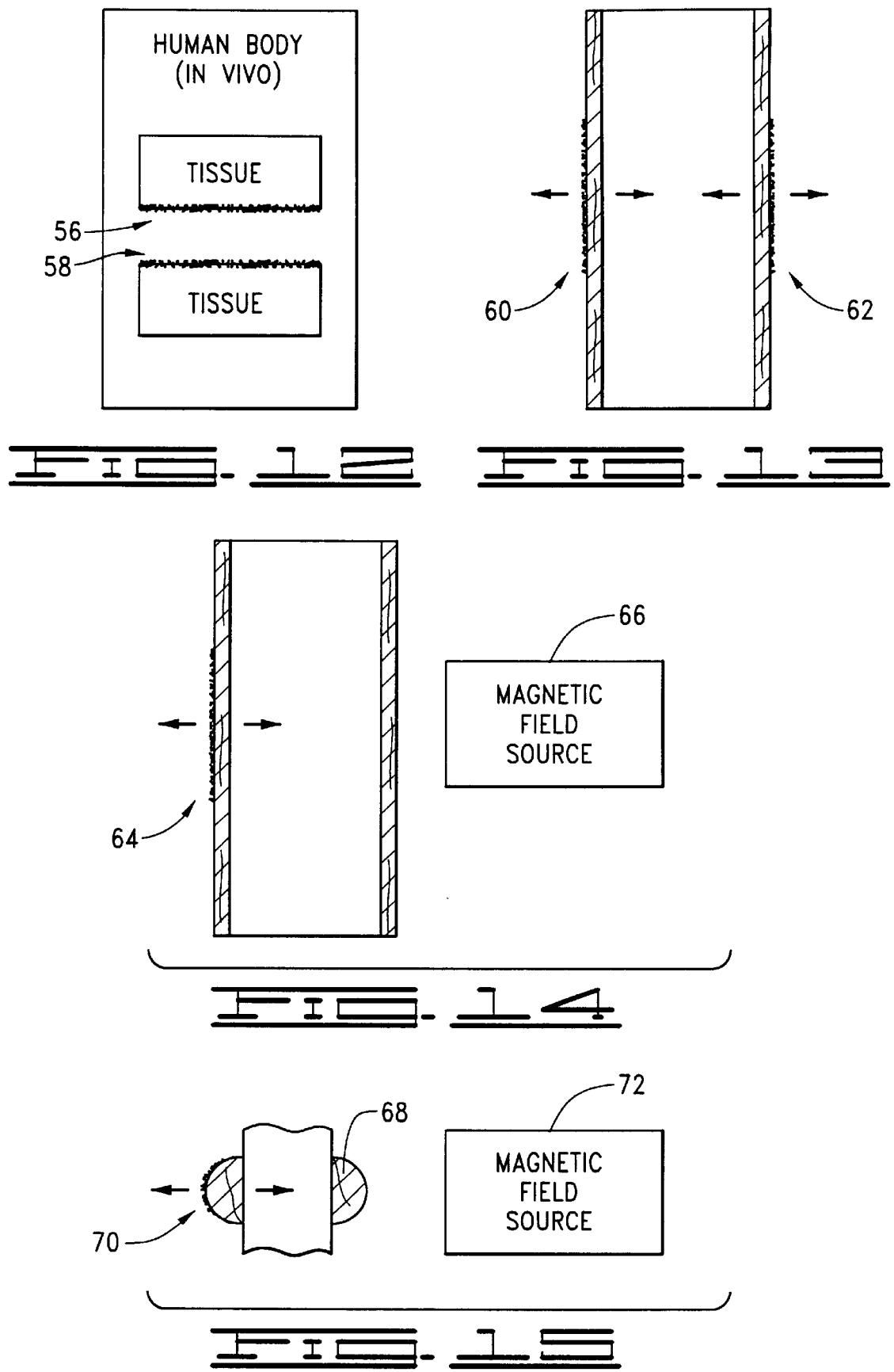

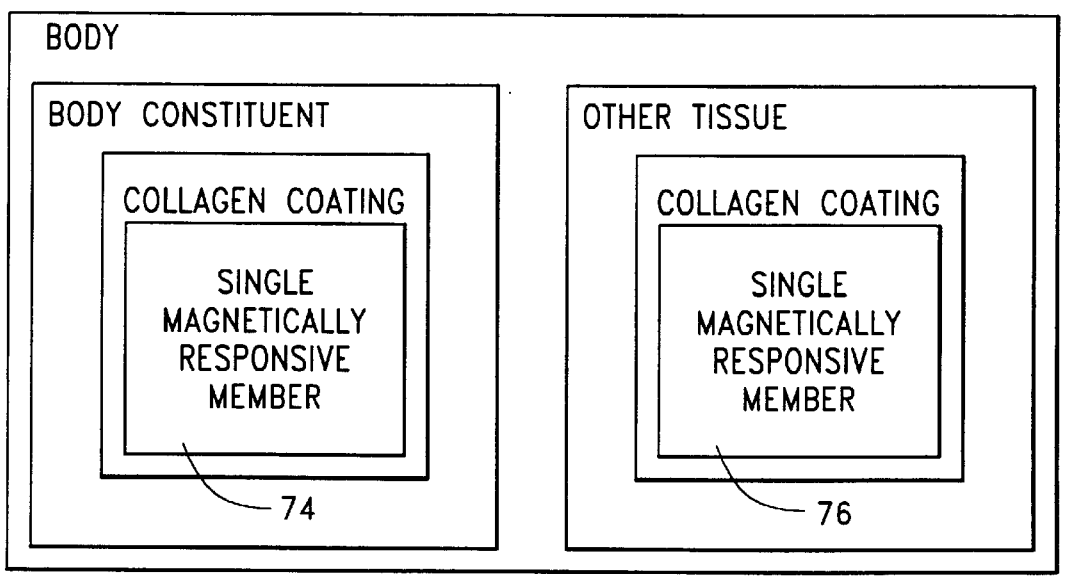
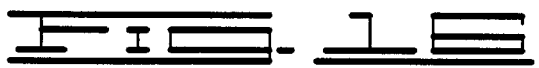
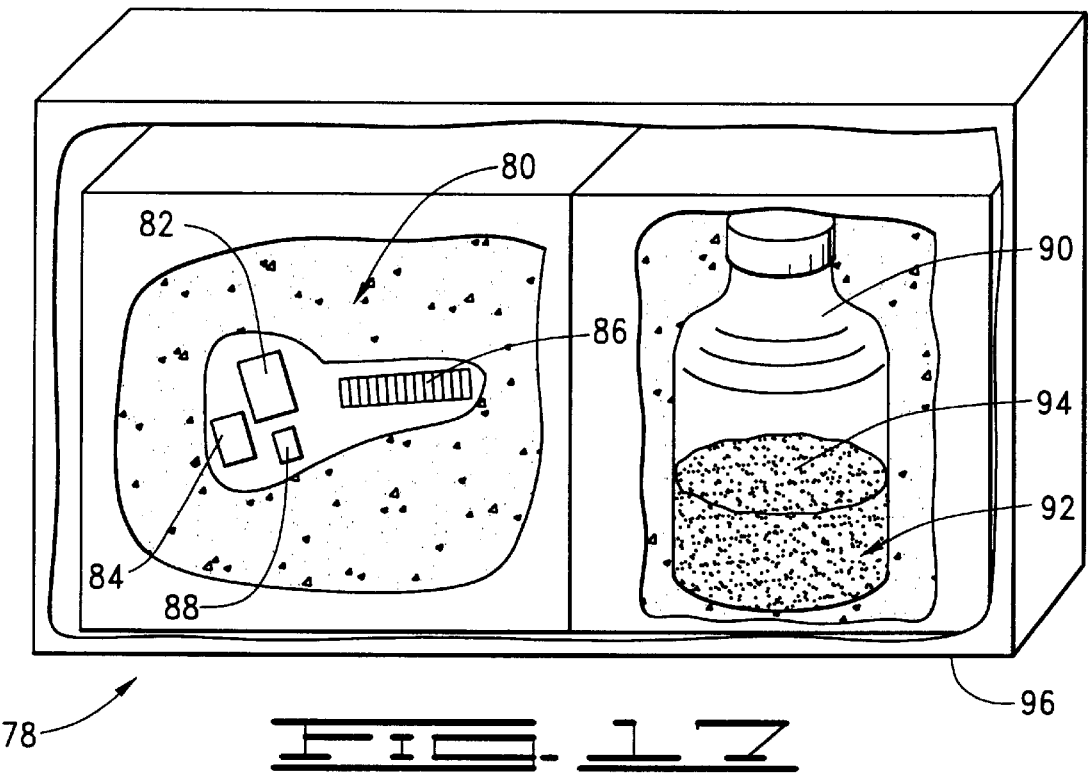

DIRECT DRIVE MOVEMENT OF BODY CONSTITUENT

BACKGROUND OF THE INVENTION

This invention relates to a bio-magnetic drive system, kit and method for moving a constituent in a human body. In a particular application, the invention relates to a hearing assist system, device and method, but a number of other applications are disclosed to exemplify the invention further. The present invention also relates to a method of connecting magnetically responsive microbeads to a constituent in a human body.

Constituents of a human body sometimes need to be moved in vivo by a force generated other than by the body itself. The constituents can be any mobile part of the body. Non-limiting examples include soft or hard body tissue, such as skin, muscle, vessels, organs, bones, connective matter, nerves, and brain mass. The movement can be with regard to achieving any desired function. Non-limiting examples include the following.

The ossicles of the middle ear are normally moved by changes in air pressure on the surface of the tympanic membrane, in the normal hearing transduction mechanism. The tympanic membrane is connected to the malleus which is connected to the incus which is connected to the stapes in the middle ear ossicular chain. When displacement of these is conveyed to the inner ear (cochlea), then the transduction is made by sensors which convert into nerve action potentials to the hearing centers of the brain. Amplification of hearing would be attained if such movements of an ossicle were amplified. In a damaged middle ear, normal ossiclar displacement or transmission does not occur and some artificial movement technique may need to be used.

The larynx as part of the vocal mechanism contains vocal folds that normally are held in apposition and with tension such that passage of air over the vocal folds produces vibration and the generation of sounds which are shaped as speech by the oral cavity. Such holding of vocal folds in apposition sometimes fails with disease and a mechanism to appose the folds would be beneficial in preserving speech. One prior mechanism includes a piece of silicone rubber surgically implanted next to the paralyzed vocal fold to wedge the vocal cords in apposition.

The eyelid must close to cleanse and protect the surface of the eye (cornea) thousands of times each day. People with motor disease or neurologic problems often have difficulty closing their eyelids and eyes become prone to infection and vision is impaired.

Wound closure for delicate plastic surgical applications is often accomplished with small sutures that require removal and often leave their own scars. If the tissue at the wound could be moved and held together without suturing, no suture scars would occur and no secondary visit to a surgeon for removal of the sutures would be needed. Preferably such closures would be more complete, providing a better barrier against infection and scarring due to infection.

In surgical applications, a surgeon may want tissue to remain in one location (for example, during the healing process, toward the natural anatomical position of the respective body part). In middle ear surgery to reconstruct the middle ear by prostheses or tissue, often large blocks of connective tissue or gelatin foam are used to form a cast to position and hold a prosthesis or operated or freed ossicle in place. This technique requires months of healing for tissue and/or gelatin foam-blood clots to be removed, so another technique for moving and holding the tissue is desirable.

The closure of sphincters in the body can fail. For example, the lower esophageal sphincter when inadequately closed allows acid reflux from the stomach and this can cause damage to the esophagus and lung (aspiration of acid). As another example, the sphincter for closure of the bladder so as to retain urine sometimes requires surgery that includes repositioning and twisting of the stomach and suturing of the lower esophageal sphincter. An improved technique for operating the sphincter could improve lives by minimizing invasive surgery.

Another sphincter application pertains to incontinence following prostate surgery. Patients can be left incontinent because of incomplete closure of the sphincter associated with the prostate. Incontinence may be the result of loss of urinary bladder control. There is the need for improved means and method for enabling closure of body openings.

Another closure application is in erectile dysfunction (ED). This is a circulatory problem where venous engorgement is required for penile erection. Presently such venous engorgement (dilation of veins and filling with blood) is accomplished by a vasodilator such as Viagra. A more cost-effective and non-pharmacological means for increasing engorgement is desirable. A means for increasing venous resistance would cause venous engorgement upstream, resulting in penile erection with the potential-elimination of impotence.

Very delicate nerve surgery where two ends of a severed nerve are sewn together is tedious, long and difficult. The sheath covering the nerve must also be restored for the nerve to live and grow. It is desirable to have some way to manipulate the severed nerve and/or its myelin sheath to cause it to be reapposed without the added insult of needle punctures and sutures adversely affecting the healing process.

Another application of the .present invention is for opening (or closing) of channels or pores or blood vessels. Such openings are important in the circulation of the body as this is the means of getting nutrients, gases and fluids to the tissues. The opening of blood vessels is accomplished normally by a pressure from within, by shear hydrostatic pressures. This does not, however, always occur. For example, if an atherosclerotic plaque is partially occluding someone's carotid artery and impedes blood flow to the head and brain, this vessel needs to be opened immediately or stroke or brain damage could occur. Atherectomy is a lengthy and dangerous procedure to remove the plaque. If, however, the lumen of the vessel could be opened easily and a person treated with lipid reducing medication, surgery on the neck could possibly be avoided and a life saved.

Although any of the foregoing, and others, could be used, assisting human hearing and moving parts of the human hearing mechanism will be used as the specific context for further describing the background of the invention and the preferred embodiments of the invention itself.

There are many different reasons why some people have hearing impairment. In general, however, sound entering the outer ear canal does not get adequately transmitted to the inner ear and/or transduced, then sent by auditory nerve. In some instances, this can be solved by amplifying the sound with a hearing aid put into the outer ear canal. In other cases, a device that electrically stimulates the auditory nerve directly needs to be implanted in the cochlea (the inner ear). In still other situations, a middle ear device that creates mechanical vibrations is needed. There have been disclosures of such middle ear devices, including magnetic, electromagnetic and piezoelectric types. A particular implementation of the present invention pertains to such middle ear actuation, and specifically magnetic and electromagnetic middle ear devices.

A person's normal middle ear includes a chain of three small bones, or ossicles. The malleus, the incus, and the stapes form this chain; and when functioning normally, these ossicles transmit mechanical vibrations from the eardrum, or tympanic membrane, at the end of the outer ear canal to the oval window, the entrance into the inner ear. When something is wrong in this ossicular chain, however, such transmission does not occur sufficiently to stimulate the cochlea and, therefore, auditory nerve. Another type of transmission deficiency occurs in sensorineural hearing loss, where some of the hair cells of the inner ear are not functioning.

One general solution to hearing problems caused by middle ear deficiencies and/or sensorineural hearing loss is to implant a magnet in the middle ear and to cause the magnet to vibrate in response to environmental sounds. The magnet is connected, for example, such that it provides enhanced mechanical vibrations to the oval window, either through an adequately functioning portion of the middle ear's ossicular chain to which the magnet is attached or through an implanted prosthesis carrying the magnet and communicating with the oval window. Greater vibration of the ossicles creates greater fluid motion in the cochlea and amplification of sounds to the person. Such is the function of implantable hearing devices, that is, greater mechanical vibratory input from the middle to the inner ear.

A number of middle ear magnet attachment devices have been proposed. Some clip to an ossicle, or part of one; others abut ossicular surfaces. Clamping or clipping onto living bone (ossicles) can compromise oxygen and nutrient delivery and cause bone erosion. Some can add mass loading to the ossicles, and some use probes that require holes placed into ossicles. Some implants are glued to living bone with a composition that may not be compatible with living bone and surface tension forces that seek to hold an implant onto the living epithelium of the round window of the inner ear. In at least one type, the eardrum is cut and the incudostapedial joint severed to allow a magnetic device to be hung on the reapposed joint. There is the need for apparatus and methodology by which the ossicular structure in the ear can be moved, but without some or all of the aforementioned shortcomings. In view of the other examples above, there is the broader need for apparatus and methodology by which other constituents in a human body likewise can be forcibly moved.

SUMMARY OF THE INVENTION

The present invention overcomes the above-noted and other shortcomings of the prior art by providing a novel and improved hearing assist system, device and method. A particular aspect of this includes a method of connecting a plurality of microbeads to an ossicle in an ear of a human; however, the method of the present invention encompasses connecting to other body constituents as well. In other broader aspects, the present invention provides a biomagnetic system, kit and method for moving a constituent in a human body. The present invention is applicable for any tissue in the body that would benefit (e.g., correctively or therapeutically) by being moved using external means other than the natural body processes that move the tissue.

The present invention enables in vivo constituents of a human body to be moved in response to forces generated other than by the body itself. Implanted collagen-coated magnetically responsive microbeads permit soft tissue to grow onto and biologically attach to the microbeads as a normal biological process. These magnetically responsive elements can then be electromagnetically or magnetically manipulated to directly, mechanically drive the body constituent(s) to which the microbeads are attached.

In the particular implementation related to hearing, the present invention facilitates implanting magnetically responsive material in a middle ear of a human. The present invention allows for biologically compatible, non-necrotizing, lightweight, encapsulated magnetically responsive material to be implanted onto the ossicular chain. This can provide reduced loading of the ossicular chain (e.g., in comparison to magnets in titanium canisters) and improved magnetic coupling. The ossicular chain does not need to be severed (thereby simplifying or reducing the surgical implant procedure), and blood supply/nutrient flow can be maintained. Such mounting may provide for lifetime implantation on all or part of an ossicular chain.

A particular implementation of the present invention can be defined as an improvement in a hearing assist system for a human ear. This improvement comprises a plurality of microbeads connected to at least one ossicle in an ear of a human. Another definition of the improvement is as a plurality of magnetically responsive microbeads connected to a constituent of the human hearing mechanism, the constituent selected from the group consisting of a tympanic membrane, a middle ear ossicle, a round window, and an oval window of a human ear.

The present invention also provides a middle-ear drive system for a human ear. This comprises a plurality of microbeads connected to a vibratory constituent in an ear of a human, and a transmitter to transmit a microbead-operative output signal within effective range of the plurality of microbeads such that the microbeads move in response.

Because the present invention has application beyond use in the middle ear, the invention can also be described as a bio-magnetic system for moving a constituent of a human body. This system comprises at least one magnetically responsive member having an attachment mechanism including collagen, the collagen bound with an epithelium of a moveable constituent in the human body.

Another definition of the present invention, as a biomagnetic drive system, includes a plurality of magnetic microbeads connected in vivo to a moveable constituent of a human body, and it also comprises a magnetic field source disposed in operative association with the microbeads but remote from the microbeads and the moveable constituent to provide a magnetic field to move the microbeads. The magnetic field source can be either inside or outside the human body.

The present invention also provides a kit for use in causing a constituent of a human body to move. The kit comprises a plurality of biologically compatible, magnetically responsive microbeads coated with a composition that connects the microbeads to a selected constituent of a human body. The kit further comprises a signal processor that includes a receiver to receive an input signal and a transmitter responsive to the receiver to transmit a magnetic output signal within effective range of the plurality of magnetically responsive microbeads. The kit also comprises a package containing the magnetic microbeads and the signal processor. The kit may further comprise a physiologic solution and a container having the physiologic solution and the microbeads admixed and contained therein, wherein the container with the admixture is disposed in the package.

The present invention also provides methods related to the above. In one definition, a method for moving a constituent in a human body comprises transmitting a signal to interact with a plurality of microbeads connected to a constituent in a human body such that the connected microbeads and constituent in the human body move in response. In another definition, the method comprises displacing with a magnetic field a plurality of magnetically responsive microbeads connected to a constituent in a human body such that the connected microbeads and constituent move in the human body. In a preferred embodiment, the microbeads are connected by collagen-integrin bonds with the constituent inside the human body. The methods defined above can further comprise selecting the constituent from the group consisting of a tympanic membrane, a middle-ear ossicle, a round window membrane, an oval window membrane, a larynx, an eyelid, a sphincter, wound tissue, surgically positioned tissue, nerve tissue, and vascular tissue of the human body.

A more particular method of the present invention aids a human to hear. This method comprises vibrating with magnetic signal transmission a plurality of magnetically responsive microbeads connected to at least one human ear constituent. The method of aiding a human to hear can also be defined as comprising: providing a plurality of microbeads in vivo to attach to at least one ossicle in an ear of a human; and processing a sound to drive the microbeads, including transmitting a signal to interact with, the microbeads such that the microbeads and the at least one ossicle vibrate in response.

The present invention further provides an in vivo method of connecting microbeads to a constituent in a human body, comprising: aspirating a plurality of magnetically responsive microbeads and accompanying physiologic solution into a syringe from an admixture of magnetically responsive microbeads and physiologic solution; inserting a needle of the syringe into the human body toward the constituent; and ejecting at least a portion of the microbeads and physiologic solution from the syringe onto or into the constituent. The in vivo method can also be defined as comprising moving a brush into an admixture of magnetically responsive microbeads and physiologic solution such that a plurality of magnetically responsive microbeads and accompanying physiologic solution adhere to the brush; inserting the brush into the human body toward the constituent; and transferring at least a portion of the microbeads and physiologic solution from the brush onto the constituent.

Therefore, from the foregoing, it is a general object of the present invention to provide a novel and improved hearing assist system, device and method. A particular aspect of this includes a method of connecting a plurality of microbeads to an ossicle in an ear (or to another suitable constituent) of a human. It is a broader object, however, to provide a biomagnetic system, kit and method for moving a constituent in a human body. Other and further objects, features and advantages of the present invention will be readily apparent to those skilled in the art when the following description of the preferred embodiments is read in conjunction with the accompanying drawings.

BRIEF DESCRIPTION OF THE DRAWINGS

FIG. 3 is a block diagram representing a signal processor that has both a receiver, to receive an external signal, and a transmitter, to transmit an actuating signal to microbeads on a constituent.

FIG. 4 is a block diagram of a signal processor in a hearing assist system having microbeads connected to an ossicle in a middle ear of a human.

FIG. 10 is a block diagram representing another embodiment of the present invention including a motor-driven permanent magnet inside or outside a living human body.

FIG. 11 is a block diagram representing another embodiment of the present invention including a permanent magnet inside or outside a living human body.

FIG. 12 represents application of the present invention in tissue-to-tissue movement.

FIG. 13 represents a vessel (e.g., a vein) to which microbeads are attached for use in accordance with the present invention.

FIG. 14 represents another embodiment of the present invention used with vascular tissue.

FIG. 15 represents a sphincter with which an embodiment of the present invention is used.

FIG. 16 is a block diagram illustrating one or more single member embodiments of the present invention.

FIG. 17 illustrates a kit of the present invention.

DETAILED DESCRIPTION OF THE INVENTION

Figure 1:
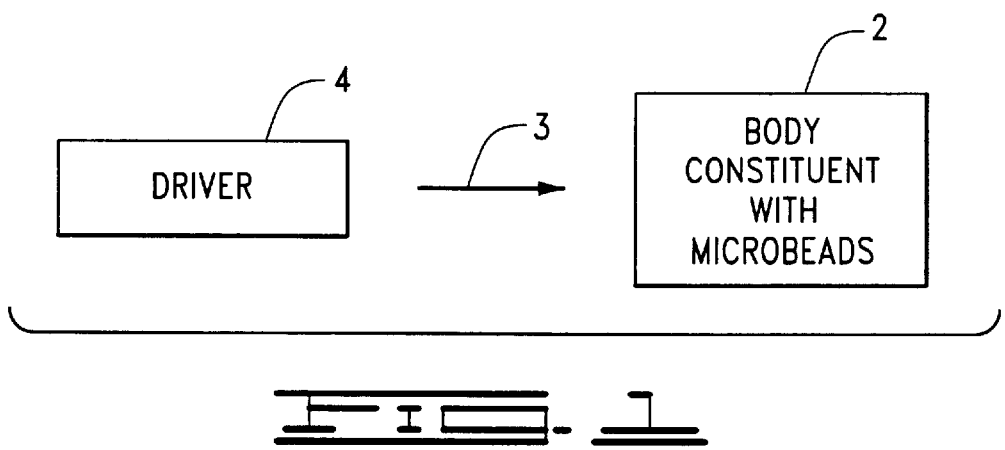
FIG. 1 is a block diagram representing a driver and a constituent of a body to which have been attached microbeads that move in response to operation of the driver.

The present invention permits a constituent (i.e., one or more constituent if consistent with desired functionality) of a human body to be directly driven into some form of movement in response to a signal generated other than by the body itself The example most referred to above is the electromagnetic driving of an ossicle of a middle ear of a human; however, any tissue in the body that would benefit (e.g., correctively or therapeutically) by being moved using external means other than the natural body processes that move the tissue may be suitable for the present invention. Other examples of such constituents include other vibratory constituents of the human ear (including the tympanic membrane (eardrum), round window membrane, and oval window membrane), vocal folds of the larynx, eyelid, wound tissue, surgically positioned tissue, sphincters, vascular tissue, and nerve tissue of the human body. Particular uses are exemplified above in the background of the invention.

There are several possibilities for generating the forces for wound closure, reapposition of tissue and mechanical movement of these, and other, body constituents. Preferred embodiments include one or more magnetically responsive beads. Particular examples include nonmagnetized, magnetically responsive, microbeads being affected by a remote or nearby electromagnet or permanent magnet or the beads themselves being magnetized as north or south and having immediate attraction to or repulsion from each other. Magnetic devices creating forces on the microbeads can be from some device inside of the body and close to the microbeads (as in the specific ear device application) or the force generating magnetic field can come from outside of the body. This can be in the form of a magnetic field that can be shaped to affect the beads in generating a force in a specific direction, for example. In general, a magnetic field source and one or more magnetically responsive members are used. "Magnetically responsive" includes materials that react to magnetic or electromagnetic fields but do not themselves inherently provide magnetic fields, and they also include materials that are themselves magnetic. Examples include ferromagnetic and paramagnetic materials, with the former preferred. Other examples include magnetic materials that inherently provide magnetic fields (e.g., rare earth magnetic materials).

That which adapts the aforementioned body constituents to be used with the preferred embodiment of the present invention is a capsule or covering of soft tissue. Specifically in the middle ear embodiment, the soft tissue is an epithelial coating provided by middle ear mucosa, to which collagen will naturally bond through integrins, which are receptors located on the surface of the cells of the mucosal epithelium. It is, however, contemplated that other bonding mechanisms can be used (e.g., genetic means of inducing other cell to cell bonding mechanisms).

Given the adaptability of the aforementioned body constituents to the present invention, microbeads are attached to the part or parts to be moved. Microbeads are known products; the type of the preferred embodiments of the present invention include ferromagnetic particles ($Fe_2O_3$) (e.g., 5 micrometers in diameter) inside pinhole free encapsulating beads. The encapsulation is to be a type of material and coverage so as to provide protection against body fluids and be biocompatible (preferably both for the lifetime of the user). Glass (a type for use in a human body) is one such material. Technology exists for coating the beads with collagen (e.g., commercially available Vitrogen 100) using recombinant DNA techniques. The collagen attaches to the epithelium of the target tissue by natural cell proteins called integrins. The beads remain associated with molecules which link the extracellular matrix of cells to the constituent cell's cytoskeleton. The beads may become internalized into the tissue itself. Such internalization into soft tissue is preferable to only cell surface attachment, as the beads are to be mechanically vibrated to generate force on the ossicles of the middle ear. Such soft tissues include epithelia, of various types, fibrous connective tissue and others, each of which may have variations on cellular connection proteins. The epithelial integrins are the most understood at this time and there has been demonstrated connection for generation of forces on in vitro cells. See, "A Novel Technique for Investigation of Mechanotransduction in Airway Epithelial Cells," D. Tschumperlin, M. Swartz, N. Wang, R. Kamm, J. Drazen, and J. Fredberg, BED-Vol. 42, 1999 Bioengineering Conference, pp. 521–522 (ASME 1999); and "Integrin-Cytoskeleton Linkages are Important Pathways for Mechanotransduction," N. Wang, BED-Vol. 42, 1999 Bioengineering Conference, pp. 523–524 (ASME 1999); both of which are incorporated herein by reference. A commercial source for microbeads is Miltenyi Biotech Inc. of Auburn, Calif. and it is contemplated that suitable encapsulation materials and technique can be readily implemented in place of typical polystyrene coated beads.

The aforementioned body constituents and microbeads, and their interconnection, are represented in FIG. 1 by the block marked with reference numeral 2. These microbeads and the body constituent(s) to which they are attached are caused to move by a drive signal 3 output from a driver 4.

Figure 2:
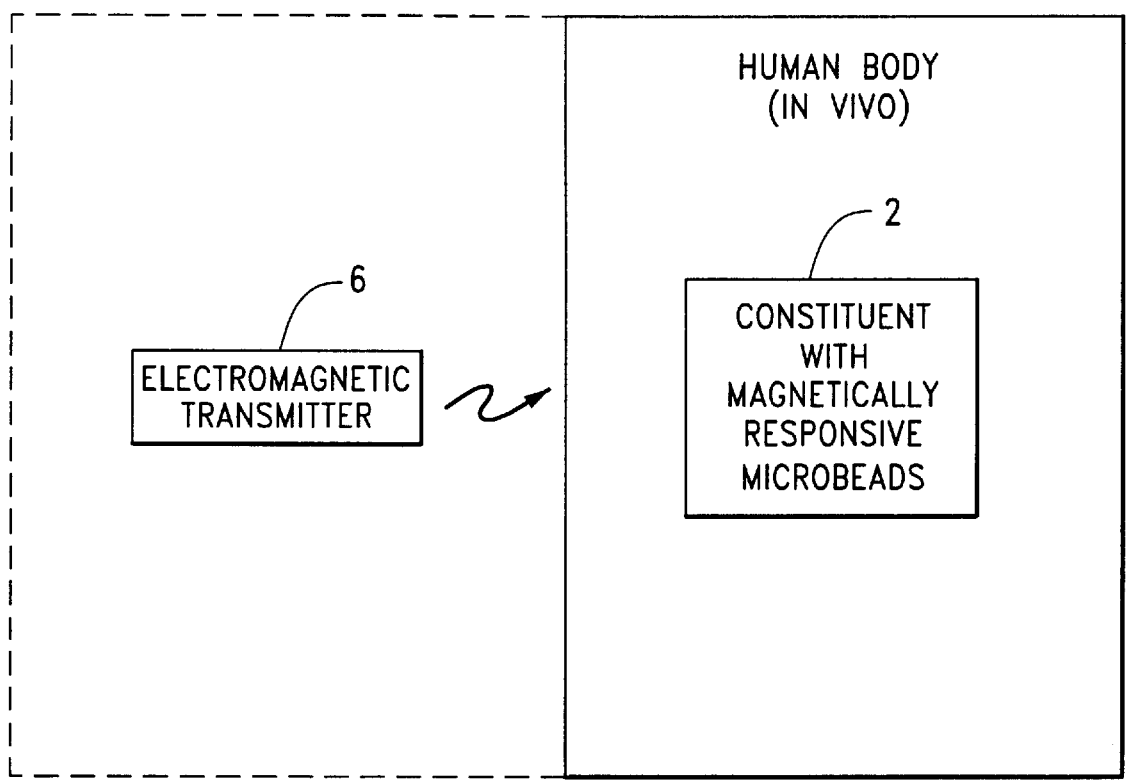
FIG. 2 is a block diagram representing an electromagnetic transmitter inside or outside a living human body having a constituent to which magnetically responsive microbeads are attached.

One preferred type of driver outputs an electromagnetic signal and so is marked as electromagnetic transmitter 6 in FIG. 2. Such a transmitter can be part of an analog or digital or hybrid (i.e., combination of analog and digital processing) signal processor 8 shown in FIG. 3 as also including a receiver 10. In a particular embodiment shown in FIG. 4, the signal processor can be of the type used with other middle ear drive or inner ear drive systems. The implementation of FIG. 4 includes a microphone 12 that generates an electric signal in response to ambient sound picked up by the microphone. A sound processor 14 takes the electrical signal representing ambient sound and modifies it (e.g., by known signal compression filtering and noise canceling techniques). The conditioned signal output by the sound processor 14 is amplified by a power amplifier 16 to drive a coil 18 at the conditioned frequencies, amplitudes, etc. The alternating current auditory signal output from the amplifier 16.drives the coil 18 to generate electromagnetic signal 20. The time varying drive signal 20 is a changing electromagnetic field that causes the magnetic microbeads to vibrate and thereby move the combined body constituent/microbead structure 2', which structure 2' in the FIG. 4 embodiment is a middle ear ossicle to which the microbeads have been attached. The created movement corresponds to the received sound and thereby produces the perception of sound. A particular implementation of the foregoing is illustrated in FIG. 5.

Figure 5:
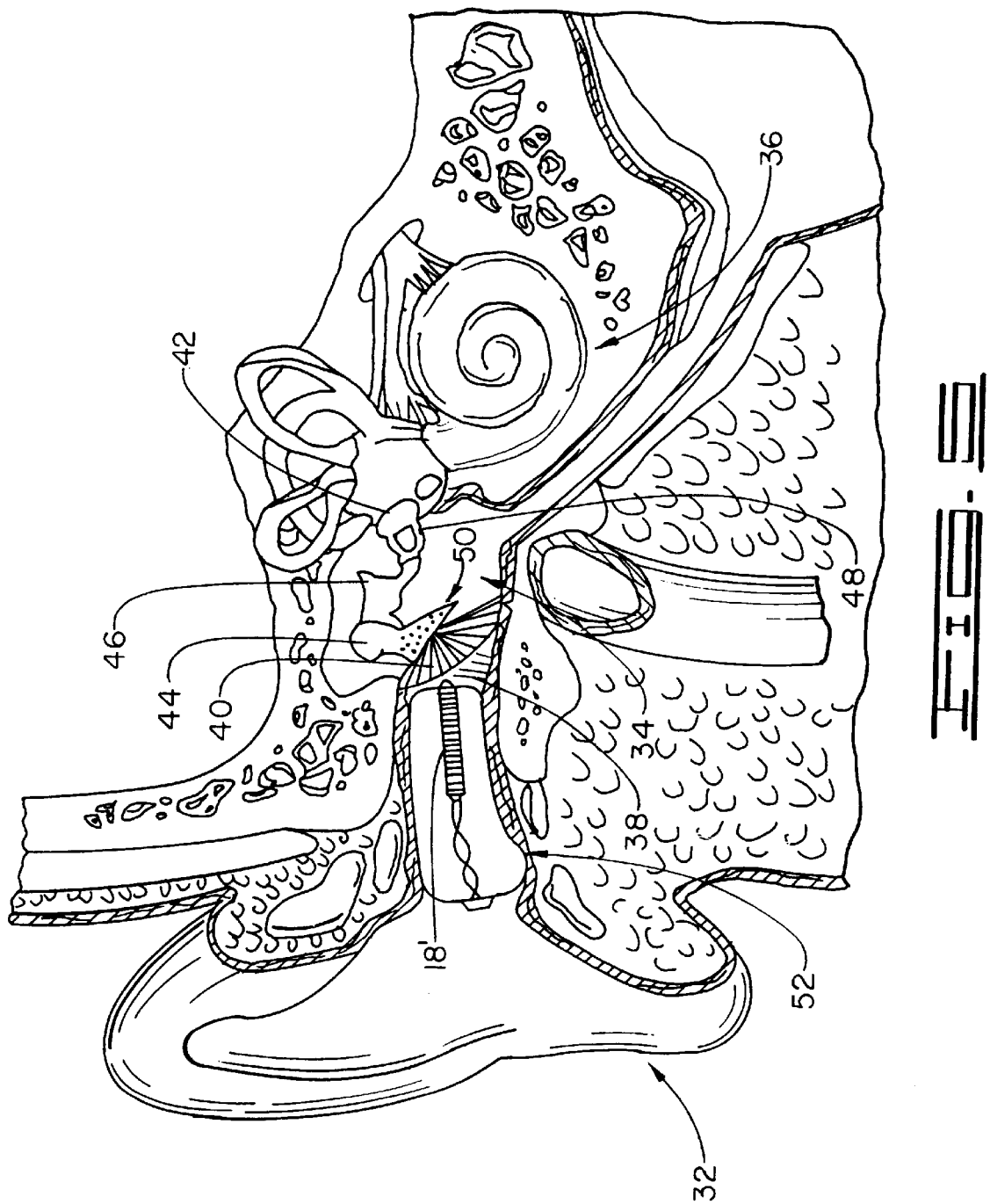
FIG. 5 is an illustration of portions of a human ear with which a hearing assist system of the present invention is used.

A human ear is represented in FIG. 5. It includes an outer ear 32, a middle ear 34, and an inner ear 36. The outer ear has an outer ear canal 38 which is normally closed at its inner end by tympanic membrane, or eardrum, 40. Also pertinent is an ossicular chain, which if intact extends from tympanic membrane 40 to oval window 42 defining an entrance to the inner ear 36. The intact ossicular chain extends through the middle ear 34 and includes a malleus 44, an incus 46, and a stapes 48. A properly functioning ossicular chain transmits vibrations from the tympanic membrane 40 in series through the malleus 44, the incus 46 and the stapes 48 to the oval window 42. Vibrations at the oval window stimulate the inner ear 36 whereby the person perceives the sound received in the outer ear 32.

With regard to the illustration of FIG. 5, it is assumed that the inner ear 36 responds to vibrations, or is made to respond, properly whereby a goal of the depicted embodiment of the present invention is to provide the vibratory stimulation to the inner ear 36 when there otherwise is inadequate vibration transmission in the person's middle ear 34. To accomplish this, the present invention provides implanted microbeads 50 for the middle ear in this example. The magnetic microbeads 50 are biologically attached, in the collagen/integrin manner described above and in the articles incorporated herein by reference, to the mucous membrane covering of any functional part of the ossicular chain communicating with the oval window. In the FIG. 5 illustration, the microbeads 50 are connected to the. malleus, preferably in alignment with the longitudinal axis of the coil 18' represented in the drawing. This technology provides the magnetic microbeads and the coating of such microbeads with collagen such that the natural collagen is recognized by the living tissue on the ossicular chain, whereby natural bridges (attachment bonds) are formed with the collagen surface to attach the microbeads to the mucosal (epithelial surface). Such attached magnetic microbeads provide for omnidirectional response to the driver signal. In FIG. 5, this driver signal comes from a signal processor in the form of an electromagnetic coil and ear mold unit 52 of a known type. This sound processor responds to received environmental sounds by generating an electrical signal that drives a coil to propagate an electromagnetic signal. The latter signal drives the microbeads in an auditory range. Such mechanical motion produces the perception of sound as the result of standing waves produced in the fluid of the inner ear.

Figure 6:
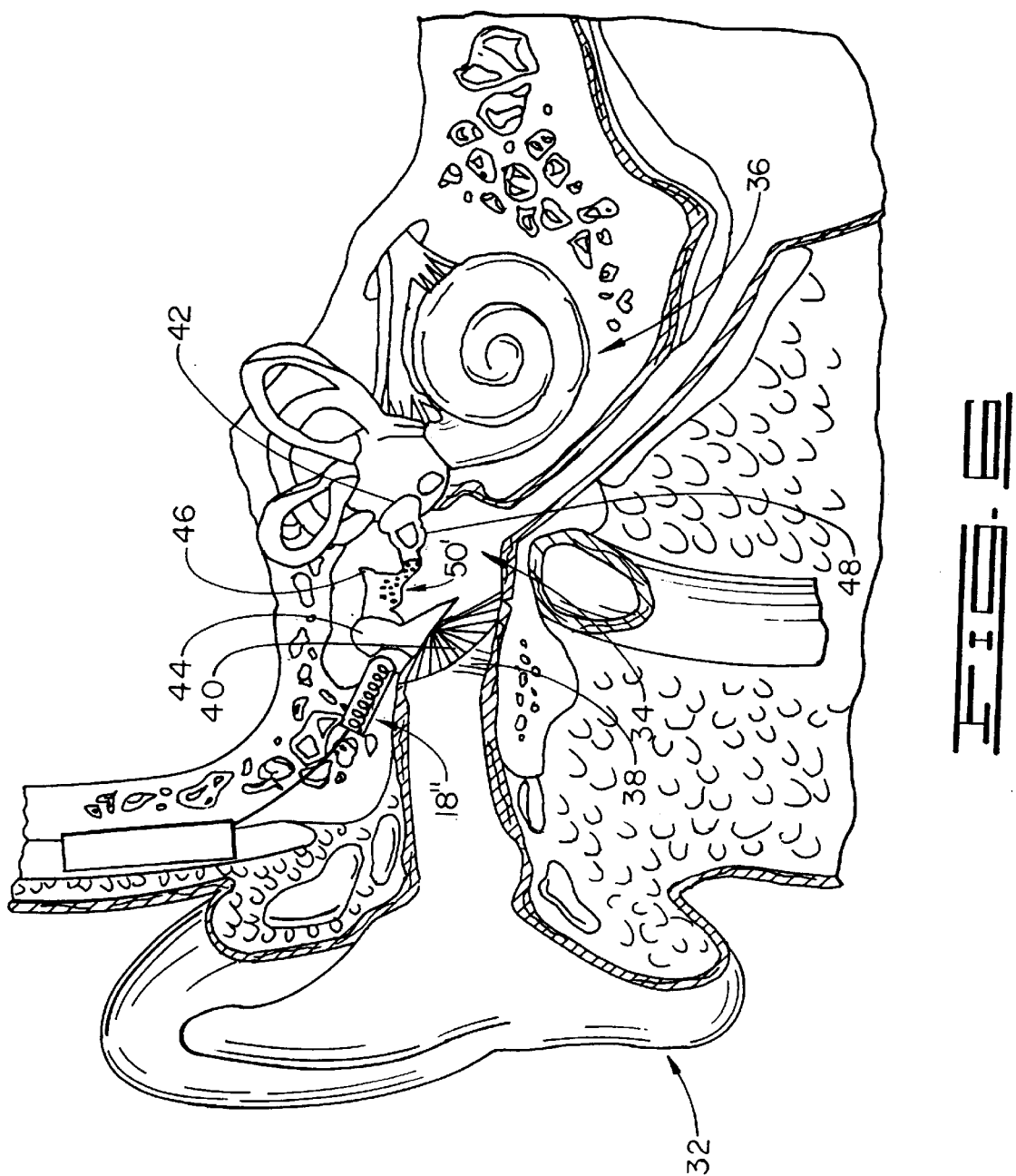
FIG. 6 is an illustration of portions of a human ear with which a hearing assist system of the present invention is used at a different locus from that shown in FIG. 5.
Figure 7:
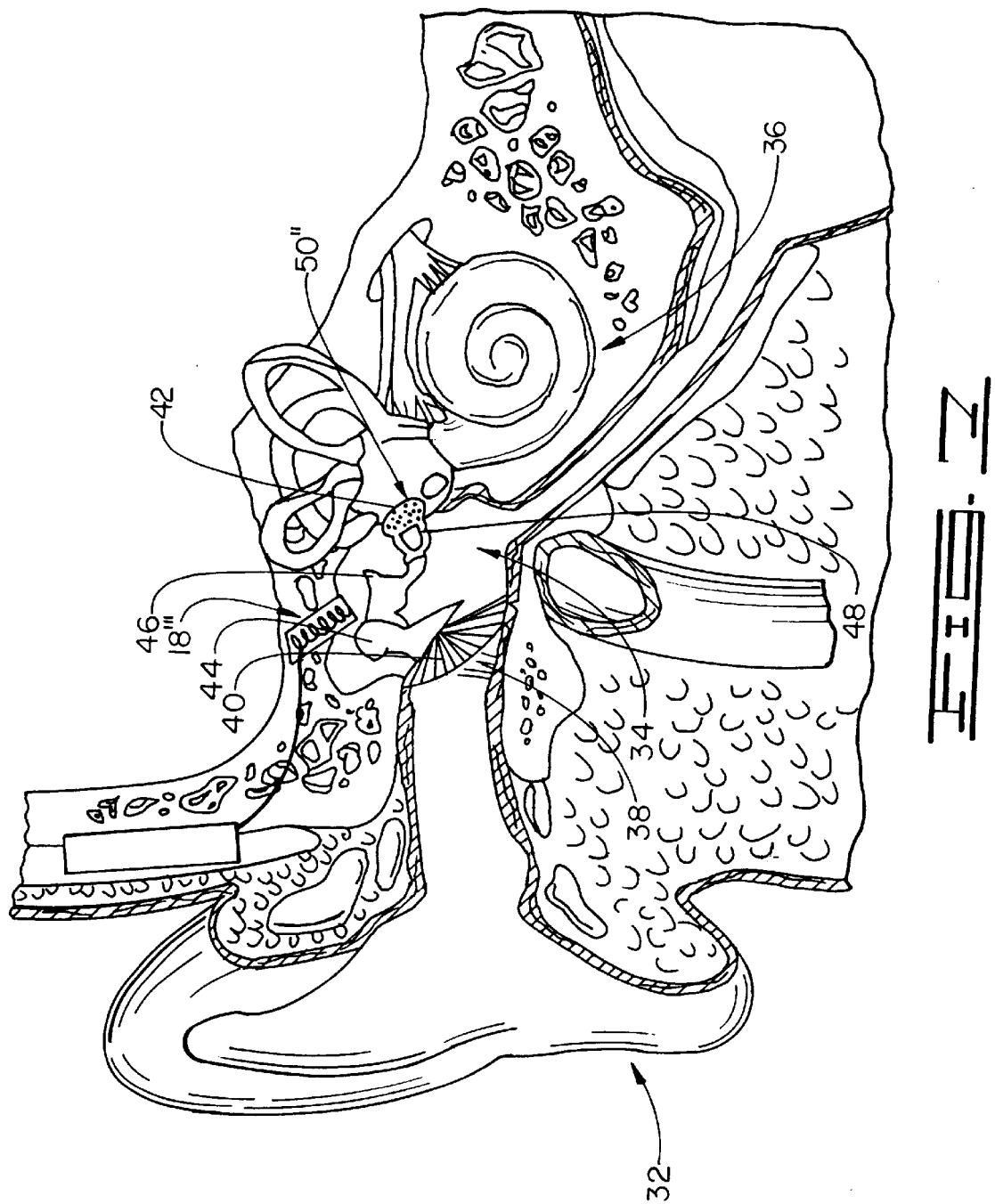
FIG. 7 is an illustration of portions of a human ear with which a hearing assist system of the present invention is used at still another site different from those shown in FIGS. 5 and 6.
Figure 8:
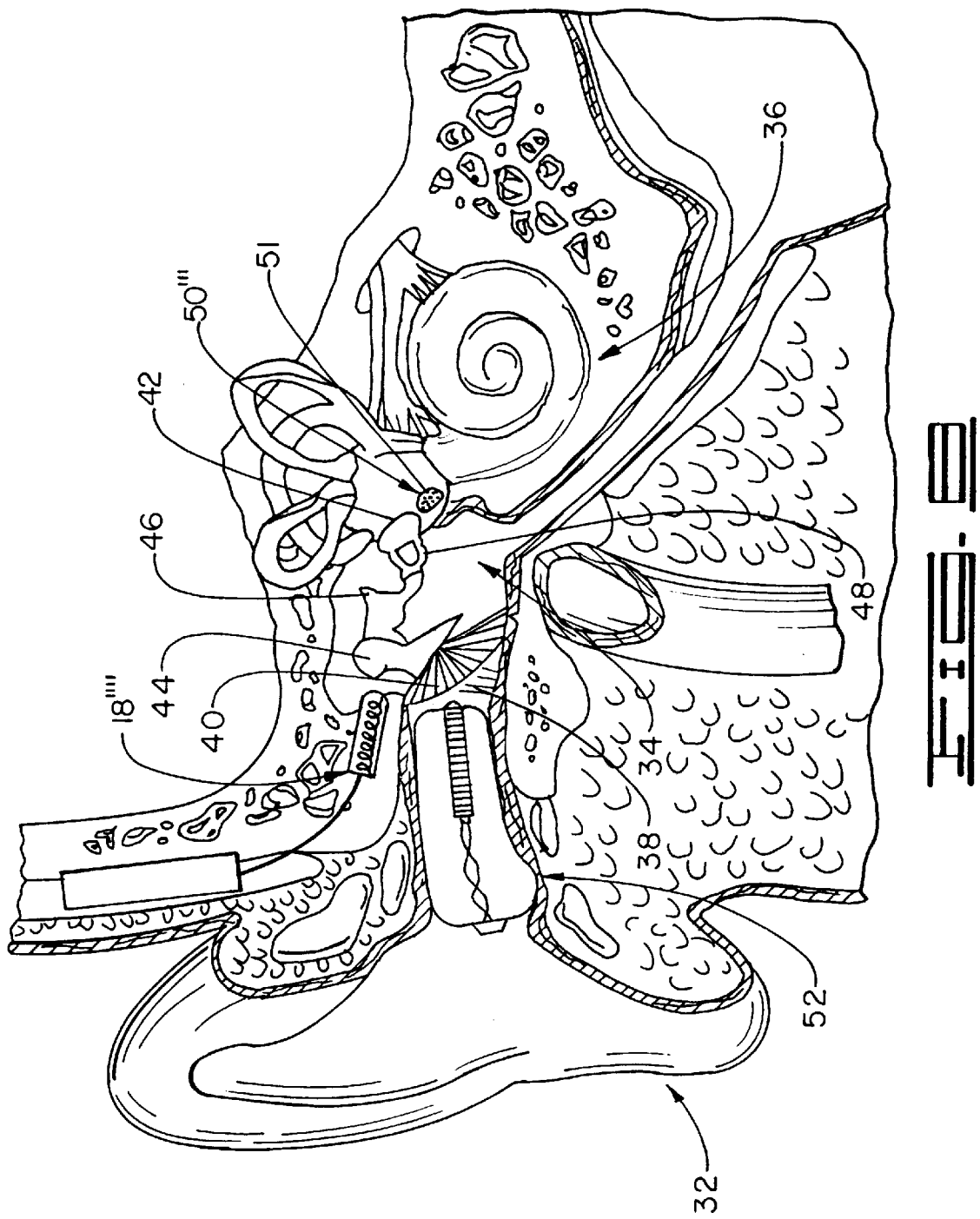
FIG. 8 is an illustration of portions of a human ear with which a hearing assist system of the present invention is used at a further locus different from those shown in FIGS. 5–7.
Figure 9:
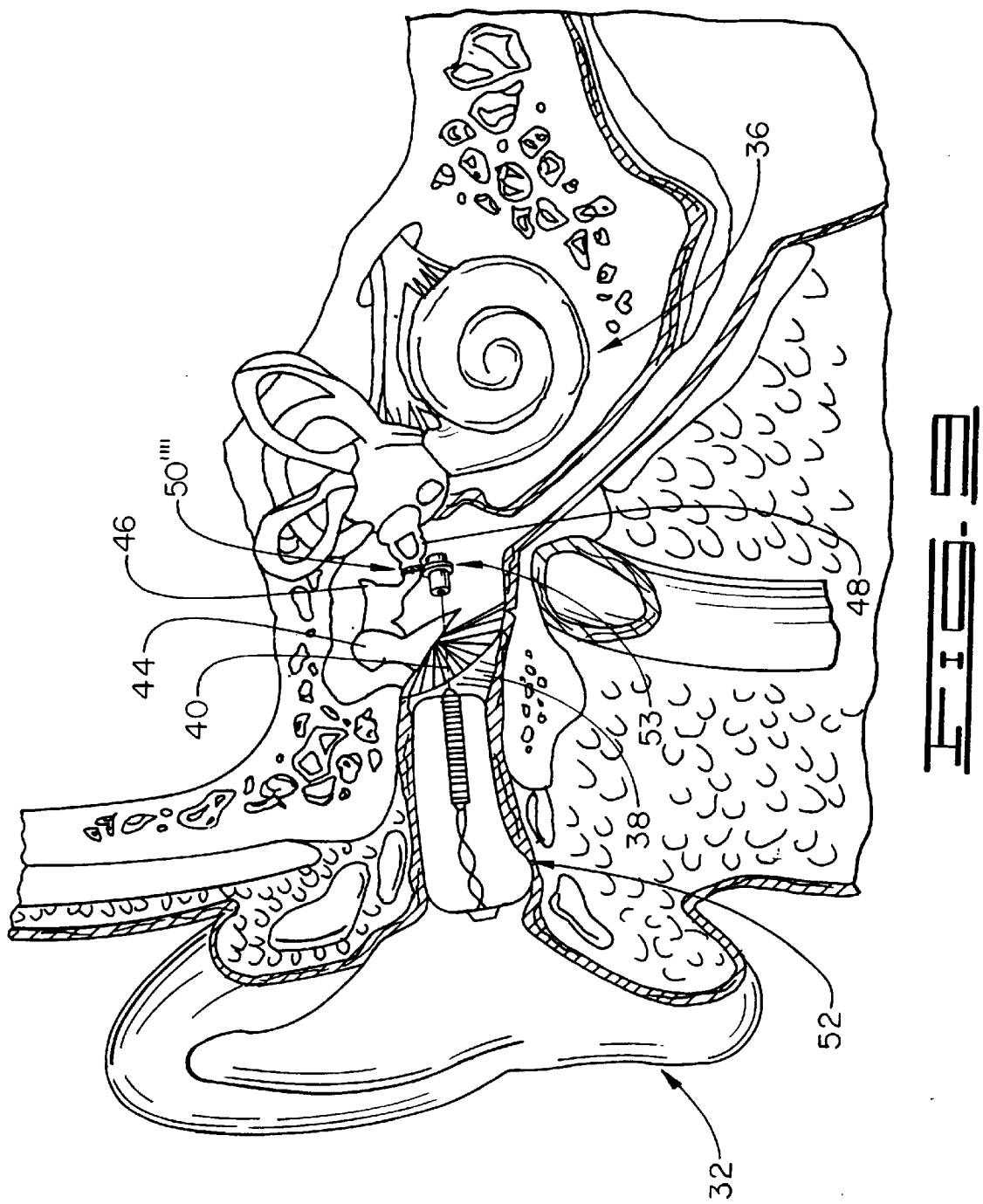
FIG. 9 is an illustration of portions of a human ear with which a hearing assist system of the prevent invention is used in conjunction with another middle ear hearing assist device.

Other examples of the present invention as used with the human ear are shown in FIGS. 6–9. FIG. 6 shows an implanted signal processor (with coil 18″) which drives microbeads 50' connected to the incus of the ossicular chain. FIG. 7 shows an implanted signal processor (with differently positioned coil 18′″) which drives microbeads 50″ connected to the oval window membrane of the ear (in this embodiment, as well as others, microbeads should not be on other constituents (e.g., an ossicle as well as the oval window membrane) if that produces conflicting movement; however, if consistent with desired function, the microbeads can be on one or more constituents). FIG. 8 shows an implanted signal processor (with. suitably positioned coil 18″″) which drives microbeads 50′″ connected to the round window membrane 51 of the ear. FIG. 9 shows a middle ear device 53. described in co-pending U.S. patent application Ser. No. 09/248,564, now U.S. Pat. No. 6,277,048 incorporated herein by reference, to which microbeads 50″″ have been attached to improve the connection of the implanted device to the incudo-stapedial joint. At least the inner surface of the incudo-stapedial attachment element of the middle ear device is coated with collagen such that it bonds with the epithelium to hold the position of the implant, as determined by the surgeon at the time of implantation, during the healing process. The microbeads also add to the magnetic responsiveness to the drive signal. Positioning (location and orientation) of the signal processor and microbeads (and other magnetically responsive material, if any) is preferably such as to optimize the signal coupling with, and resultant movement of, the microbeads (and other magnetically responsive material, if any).

As used in this specification and the claims, reference to particular parts, such as an ossicle or ossicular chain, includes portions thereof as well as the whole of the part. For example, referring to microbeads as attached to an ossicle encompasses attachment across the entirety of an ossicle and on or in only a portion of an ossicle as well as on other ossicles or portions thereof; thus, a coating of microbeads could be on less than an entire ossicle, or on multiple ossicles simultaneously.

An alternate driver for implanted microbeads which are integrated into and attached to the surfaces of cells is a permanent magnet providing a static magnetic field. The static field may be used to vibrate the microbeads and attached body constituent; this can be by moving the magnet by a connected motor, for example, as illustrated in FIG. 10. In this drawing a magnet 55 is moved back and forth (away from and towards the microbeads) by a motor 54. The movement of the magnet 55 by the motor 54 can be at auditory frequencies such as for the aforementioned hearing applications or at some designated frequency for other applications (for example, a slow pulsing frequency for the sphincter opening from the urinary bladder). For a specific example, a piezoelectric bender bimorph mechanical driver has a magnet attached to the end of the bender bimorph and this magnet moves in desired frequencies in close proximity to the implanted microbeads. Thus a DC magnetic field is influencing the magnetically responsive microbeads. The movement back and forth of the magnet varies the strength of the magnetic field and therefore the movement of the microbeads. This is not an attraction-repulsion type of driving that would be experienced with a reversing electromagnetic field. There is in this case a greater then lesser then greater, etc., attractive force of the moving magnet that is influencing the microbead population. The greater the population of the microbeads, the greater the forces of attraction for either of the driving mechanisms above.

As another example, the remote magnetic field can come from a suitably sized magnet 55' that collectively attracts the microbeads and induces a force in a single direction (see FIG. 11). One application for this is for the closure of the veins exiting the penis to compensate for erectile dysfunction.

A non-time varying electromagnetic field can also be used as a static magnetic field source (e.g., a direct current can produce a static electromagnetic field).

The foregoing examples pertaining to hearing have been stated with regard to assisting hearing impaired individuals. The present invention has other hearing applications even for ones who have no hearing impairment. For example, it may be used in the area of hearing protection. People working around very noisy sites (e.g., jet engines) may wear an existing form of protection against noise-induced hearing loss. They wear headsets that produce sounds 180 degrees out of phase with (i.e., in opposition to) the ambient noise, thus canceling out each of the two sounds such that movement of the ossicles is neutralized, protecting the ear from damage by overdrive. It is contemplated that ossicles coated with microbeads may be more effectively neutralized by anti-movement produced electromagnetically or magnetically. This would be a non-obtrusive implant onto the ossicles (i.e., presence of the microbeads would not interfere with normal hearing processes because the mass loading would be so small, such as less than 20 milligrams). On the other hand, such people would also be susceptible to stray environmental electromagnetic fields, but this is not contemplated to be a serious drawback for the anti-noise hearing protection.

Another specific application is that the microbeads may provide a covert means of communicating with an individual by auditory means. Presently, secret service and security personnel communicate by wireless microphones placed into their ear canals. A transmitter sends a signal to a receiver which then activates a speaker in the ear canal. With the microbeads on an ossicle, a room encircled with an electromagnetic coil could covertly and secretly communicate to an individual without anyone else being aware of it. There would be no "giveaway" of an object, visible in a person's ear canal. The person would be hearing normal sounds as well as the covert communications. Furthermore, if a room prepared for covert communication is not available, an individual could wear a large electromagnetic coil under his or her clothing such that a remote signal could be received from another source and the hidden body coil activated and the microbeads moved to produce sound. This coil under the clothing was the basis of the Ear Lens technology from Resound Corp. The Ear Lens was a heavy magnet stuck onto the tympanic membrane by surface tension forces (drop of oil on a silicone rubber diaphragm to which was attached the magnet).

Referring next to FIGS. 12–15, examples of other applications of the present invention will be given; however, these are not limiting of broader aspects of the invention.

FIG. 12 represents cases involving tissue to tissue movement. Particular examples include:

(1) The larynx as part of the vocal mechanism contains vocal folds that normally are held in apposition and with tension such that passage of air over the vocal folds produces vibration and the generation of sounds which are shaped as speech by the oral cavity. Such holding of vocal folds in apposition can be achieved with the present invention, such as by using two pluralities 56, 58 of oppositely polarized magnetic microbeads that are placed on the folds to be apposed so that the two pluralities of microbeads move toward each other due to the attractive polarities.

(2) The eyelid must close to cleanse and protect the surface of the eye (cornea). A bio-magnetic mechanism as described above for the larynx can be used to hold an eyelid closed or open. One of the pluralities of microbeads is connected to the eyelid and the other either below the eye (to close) or above the eye (to open).

(3) Wound closure can be obtained by connecting such oppositely polarized magnetic microbeads 56, 58 on opposite sides of the open wound tissue so that the attractive magnetic fields pull the microbeads and connected tissue together.

(4) In surgical applications, often a surgeon wishes tissue to remain in one location during the healing process (e.g., toward the natural anatomical position of the respective body part). With a magnetic retaining by the magnetic microbeads, positioning can be obtained and maintained. One of the pluralities of microbeads is connected to the constituent to be positioned and the other plurality of microbeads is connected to tissue at the site where the constituent is to be retained.

(5) Nerve surgery where two ends of a severed nerve are sewn together is tedious, long and difficult. The sheath covering the nerve must also be restored for the nerve to live and grow. Using the present invention, on the other hand, the polarized microbeads 56, 58 can be placed on the ends of a severed nerve and/or its myelin sheath causing the ends to be reapposed.

FIG. 13 represents two pluralities 60, 62 of magnetic microbeads connected to vascular tissue. If the microbeads are of the same polarization, repulsion occurs so that the diameter of the lumen of the vessel enlarges (indicated by the outer set of arrows). If the microbeads are of different polarities, attraction occurs so that the lumen diameter decreases (as indicated by the inner set of arrows pointing towards each other). This latter technique can be useful where venous engorgement is required for penile erection. A temporary venous output blockage can be caused by providing a force on the venous outflow tracks. Such increased venous resistance (by the bio-magnetic closure means) causes venous engorgement upstream and penile erection with the potential elimination of impotence. The former technique (using a repulsive force) can be used for opening vessels, channels or pores. Such openings are important in the circulation of the body as this is the means of getting nutrients, gases and fluids to the tissues. The opening of blood vessels, for example, is accomplished normally by a pressure from within. However, blood vessels could be opened further in diseased states such as atherosclerosis, by the pushing apart of the external vessel wall or the Adventist surrounding a blood vessel. Another example for use in opening blood vessels is with arteries that feed the penis to thereby increase inflow into the corpus cavernous (erectile tissue). The foregoing can also be achieved by using one set of microbeads 64 and a discrete magnetic field source 66 (e.g., a permanent magnet or an electromagnet) as represented in FIG. 14. The relative polarizations and positioning of the magnetic field source determine the direction of movement. Opening and closing movements can be achieved with other microbead/magnet combinations as well (e.g., two magnets, each creating an outward pulling force on a respective set of microbeads).

Another particular example is represented in FIG. 15. This illustrates a sphincter 68 having microbeads 70 connected :to one region of it. A magnetic field source 72, such as mentioned above for magnetic field source 66, can be used to control the sphincter to close or open the channel around which the sphincter is located. Specific, but non-limiting, examples include the lower esophageal sphincter, the sphincter for closure of the bladder, and urethral usage for incontinence following prostate surgery.

A particular example of using the present invention will be described next with reference to connecting the microbeads to an ossicle in the middle ear.

In a sterile culture medium a suitable quantity of glass coated beads (e.g., 10,000) is coated with 50 mg (milligrams) of collagen that is commercially available (e.g., Vitrogen 100). The coated beads are stored in physiologic solution and temperature in sterile vials for protection until surgical application. A physiologic solution is preferably one that has the same pH and chemical environment as the intrinsic body fluid. A physiologic temperature is one at which life can be maintained, and preferably one at which collagen can survive in the preferred embodiment.

The slurry of microbeads in physiologic solution may also contain a biological "enhancer" to facilitate and accelerate the attachment of beads to the cells of the mucosae. Such enhancer would be some substance that would make the slurry sticky by either surface tension forces or sticky in the glue sense, such as fibrin glue added to the slurry. Fibrin glue is a clinical product (widely used in Europe) where the natural fibrin from humans is concentrated and used for holding things in place in the body (e.g., holding ear prostheses in place during the healing process). The fibrin glue is removed by natural healing processes over time (e.g., 2–4 weeks), as scavenger cells called macrophages ingest the fibrin as it breaks down. The collagen is not ingested, and when exposed to the surface of the mucosa of an ossicle, it attaches. The preferred embodiment is for the attachment to take place instantaneously with first contact of the beads with the cell surface; however, practical attachment via collagen/integrin bonds takes hours to days. The quantity of beads placed is dependent on desired magnetic attraction and percent retention of beads by the cells. It is also surface area limited, so the preferred application is for maximum application on the entire surface of the mucosa, closest to the electromagnetic coil or other magnetic field source.

In the operating room a surgeon elevates the tympanomeatal flap (eardrum) using standard surgical technique, under local anesthesia. The ossicles are then visualized under an operating microscope and the beads are aspirated into a microsyringe with long needle for placement onto the surface of an ossicle. The needle is introduced through the opening into the middle ear space, under direct visualization, and the surface of an ossicle is covered with the solution containing beads. This is accomplished by ejecting the physiologic solution containing the microbeads ( a slurry of microbeads) onto the surface of the selected ossicle. This is preferably the surface closest to the electromagnetic coil, wherever it is located, such that the bead population is in axial alignment with the electromagnetic coil's axis, plus or minus 30 degrees. The surface tension on the surface of the mucosa (epithelium) retains the beads while the tympanomeatal flap is closed and the procedure is complete. Total weight of the bead complex for an ossicle is preferably 2–10 mg (5 milligrams per milliliter of physiologic solution with microbeads). This is to prevent mass loading that could adversely affect natural function of the ossicle. Over the following 14–17 days the beads become attached to or integrated into the surface of the mucosal tissue. The ossicle and therefore ossicular chain is now magnetically responsive and will move in response to an applied magnetic field. The magnetic field for hearing use typically moves the microbeads and attached constituent in a vibratory manner, but in general the magnetic field is used to displace, whether vibrationally or in single-direction displacement or otherwise, the microbeads and connected constituent. The method of the present invention includes generating the various magnetic fields described above.

The following gives examples for connecting microbeads in other contexts, including those described above.

If microbeads are to be placed onto the surface of a blood vessel, a syringe needle is introduced under radiological visualization (fluoroscopy) to approach the blood vessel target. The target vessel may need to have enhanced visualization by the use of radioopaque dyes injected into the flow of the bloodstream through the vessel. With vessel visualization and upon reaching the target, content of a syringe containing the microbeads is injected near the surface of the vessel. Repeated penetrations of the skin, approaching the vessel, take place until a sufficient amount of the blood vessel surface has microbead placement and the needle is withdrawn.

In the event of placing microbeads onto veins draining the penile corpus cavernosum, a needle approach may also be used, however, no single vein is the target but rather the effluent venous complex that if occluded (at least to a sufficient partial degree) will cause upstream engorgement of the veins and enlargement of the penis. Injection of beads onto one side of the venous complex can be made such that an external magnetic field as in a DC magnet placed on the opposite side of the venous complex causes the two magnetic entities to attract each other, compress the venous complex and cause venous engorgement (erection).

For the placement of microbeads onto one or both of the vocal folds in the larynx, a simple artist's paintbrush (suitably sized and sterilized) containing the microbeads may be used to apply the beads via an oral approach. This may require several applications over time as the natural swallowing, speaking, and flow of saliva may wash some of the beads off the vocal folds. Alternatively, a temporary bonding solution may be used to hold the beads on the surface of the vocal folds for 7–14 days as the microbeads become attached. Such biological glue may be commercially available fibrin glue that is made from the fibrin extracted from blood. Fibrin is naturally broken down and removed from a site and is biocompatible.

In the event of using microbeads in the upper and lower eyelids to facilitate closure, microbeads may be injected but in this application there is no need for a target attachment site. Here the microbeads may be injected in small quantities using the same technique as in plastic surgical reconstruction when small volumes of collagen are injected under the skin for filling in defects. In this instance the microbeads may respond to an, implanted electromagnetic coil implanted in the lower eyelid on the upper face, or alternatively the microbeads may be polarized and composed of permanent magnetic material such that there will be a natural attraction between the upper and lower eyelids and the resulting force will be sufficient to keep the eye closed. One particular type of neurological lesion allows a person to open his or her eyes but not close them. With another type of eye motor control lesion, the person cannot keep the eyelids open. A similar arrangement may be made with microbeads in the subforehead region and in the upper eyelid such that the eyelid is attracted by magnetic forces upwards and the eye is maintained open.

In the event of using the forces generated by the present invention for the control of bladder function (continence), there is the need for a surgical operation to place (by either the injection technique or the brush technique) a coating of microbeads on one side of the sphincter controlling voiding of urine. An implantable electromagnetic coil can be implanted on the opposite side of the sphincter. The use of fibrin glue is favorable here such that the coating of microbeads is held in place on the mucosal surface coating the sphincter until the attachment occurs and then the fibrin is removed by natural scavengers that clean the body. An implanted electromagnetic coil is used to maintain a magnetic field, thus attracting the microbeads, thus producing a constrictive force across the sphincter, thus preventing urine from flowing out of the bladder into the urethra. Alternatively, a permanent magnet can be placed outside of the body on the opposite side of the sphincter (controlling voiding of urine) to which microbeads are permanently attached. Manual removal of this magnet by a person removes the magnetic attraction and opens the sphincter so that urine flows to empty the bladder.

In the application of beads for reapposing two cut ends of a nerve, the paint brush application is preferred. Likewise in the closing of wounds without sutures, both sides of the wound are coated with microbeads from a brush and the beads are held in place by the natural clotting at the site of wound closure. External magnets may be used to attract the wound site microbeads and so create better tissue interface forces for a better and more complete closure.

Another format of the present invention includes a whole magnet that is hermetically sealed against body fluids and then coated with collagen for attaching (e.g., to naturally bond with an epithelium of a vibratory constituent of the human ear). In other words, this provides one large bead with all the considerations given above. In the human hearing context, for example, such a magnet can be attached to an ossicle or the round window or the back side of the tympanic membrane or the front side of the tympanic membrane. Two such magnets 74, 76 can be used for holding one or more constituents such as in one or more of the examples described above (see FIG. 16).

Still another aspect of the present invention is as a kit 78 for use in causing a constituent of a human body to move. A particular implementation as a middle ear hearing assist system is illustrated in FIG. 17. This kit includes a deep canal ear mold 80 of a known type (e.g., having a compartment molded to fit in a user's outer ear canal, a sound processor 82 with an input signal receiver including microphone 84 and with a magnetic output signal transmitter (here including an electromagnetic coil 86), and a battery 88). The kit 78 also includes a container 90 (such as a jar or vial) holding a sterile solution of microbeads 92 in physiologic growth medium 94. The microbeads 92 have living collagen around glass (or other suitable material as described above) encapsulated ferromagnetic beads. These are suitably contained (e.g., in stabilizing packing material) in a suitable outer package 96, such as a box.

Thus, the present invention is well adapted to carry out the objects and attain the ends and advantages mentioned above as well as those inherent therein. While preferred embodiments of the invention have been described for the purpose of this disclosure, changes in the construction and arrangement of parts and the performance of steps can be made by those skilled in the art, which changes are encompassed within the spirit of this invention as defined by the appended claims.

What is claimed is:

1. In a hearing assist system for a human ear, the improvement comprising at least one magnetically responsive member having an attachment mechanism including collagen, the collagen configured to become naturally bonded with an epithelium of a vibratory constituent of the human ear.

2. A middle-ear drive system for a human ear, comprising:
   a plurality of microbeads for connecting to a vibratory constituent in an ear of a human, wherein the microbeads include collagen, the collagen configured to be bound to the epithelium of the vibratory constituent; and
   a transmitter to transmit a microbead-operative output signal within effective range of the plurality of microbeads such that the microbeads move in response.

3. A kit for use in causing a constituent of a human body to move, comprising:
   a plurality of biologically compatible, magnetically responsive microbeads coated with a composition for connecting the microbeads to a selected constituent of a human body;
   a signal processor including a receiver to receive an input signal and further including a transmitter responsive to the receiver to transmit a magnetic output signal within effective range of the plurality of magnetically responsive microbeads;
   a package containing the plurality of microbeads and the signal processor, and
   a physiologic solution and a container having the physiologic solution and the microbeads admixed and contained therein, wherein the container with the admixture is disposed in the package.

4. A kit as defined in claim 3, wherein the signal processor is in the form of a deep canal ear mold.

5. A method of aiding a human to hear, comprising vibrating with magnetic signal transmission a plurality of magnetically responsive microbeads connected to at least one human ear constituent, wherein the microbeads are connected by collagen-integrin bonds on the epithelium of the at least one human ear constituent.

6. An in vivo method of connecting microbeads to a constituent of an ear in a human body, comprising:
   aspirating a plurality of magnetically responsive microbeads and accompanying physiologic solution into a syringe from an admixture of magnetically responsive microbeads and physiologic solution;
   inserting a needle of the syringe into the ear of the human body toward the constituent; and
   ejecting at least a portion of the microbeads and physiologic solution from the syringe onto or into the constituent of the ear.

7. An in vivo method of connecting microbeads to a constituent in a human body, comprising:
   moving a brush into an admixture of magnetically responsive microbeads and physiologic solution such that a plurality of magnetically responsive microbeads and accompanying physiologic solution adhere to the brush;
   inserting the brush into the human body toward the constituent; and
   transferring at least a portion of the microbeads and physiologic solution from the brush onto the constituent.

8. In a hearing assist system for a human ear, the improvement comprising at least one magnetically responsive member having an attachment mechanism for naturally bonding, through cellular connection proteins, with an epithelium of a vibratory constituent of the human ear.

9. In a hearing assist system for a human ear, the improvement comprising a plurality of biologically compatible, non-necrotizing, lightweight magnetically responsive members, each of the members coated with an attachment mechanism to naturally bond through integrins on cells of the human ear.

10. In a system for inducing the perception of sound in a human, the improvement comprising a plurality of magnetically responsive beads including biological attachment means for naturally bonding with cellular connection proteins of a constituent selected from the group consisting of a tympanic membrane, a middle ear ossicle, a round window, and an oval window of a human ear.

11. A middle-ear drive system for a human ear, comprising:
   magnetically responsive material in a matrix for linking to a cell of a vibratory constituent in an ear of a human after the material and the matrix are placed on the vibratory constituent; and
   a transmitter to transmit an output signal within effective range of the magnetically responsive material such that the material and the linked vibratory constituent move in response when the magnetically responsive material is linked to the vibratory constituent and the transmitter transmits the output signal within effective range.

12. A middle-ear drive system as defined in claim 11, wherein the magnetically responsive material includes ferromagnetic material and the output signal includes an electromagnetic signal.

13. A middle-ear drive system as defined in claim 11, wherein the output signal drives the magnetically responsive material and linked vibratory constituent in opposition to ambient noise affecting the vibratory constituent.

14. A middle-ear drive system as defined in claim 11, wherein the output signal includes an electromagnetic signal generated by at least a part of the transmitter spaced from the human.

15. A middle-ear drive system as defined in claim 11, wherein the transmitter includes an electromagnetic signal generator.

16. A middle-ear drive system as defined in claim 11, wherein the transmitter includes a static magnetic field source and means for moving the source relative to the magnetically responsive material.

17. A method of aiding a human to hear, comprising vibrating with magnetic signal transmission a plurality of magnetically responsive beads connected through integrin bonds on epithelium of at least one human ear constituent.

18. A method of aiding a human to hear, comprising vibrating with magnetic signal transmission magnetically responsive material connected through cellular connection proteins to a cell of at least one human ear constituent.

19. A bio-magnetic system for moving a constituent of a human body, comprising at least one magnetically responsive member having an attachment mechanism configured to connect the member, through natural bonding with cellular connection proteins, to a cell of a moveable constituent in the human body, wherein the constituent is selected from the group consisting of a tympanic membrane, a middle-ear ossicle, a round window membrane, an oval window membrane, a larynx, an eyelid, and a sphincter.

20. A bio-magnetic system as defined in claim 19, further comprising means for vibrating the at least one magnetically responsive member.

21. A bio-magnetic system as defined in claim 20, wherein the means for vibrating includes an electromagnetic signal generator to provide an electromagnetic signal to vibrate the at least one magnetically responsive member.

22. A bio-magnetic system as defined in claim 20, wherein the means for vibrating includes a magnet and a motor connected to the magnet to move the magnet relative to the at least one magnetically responsive member.

23. A bio-magnetic system as defined in claim 19, further comprising means for moving the at least one magnetically responsive member into a held position.

24. A bio-magnetic system as defined in claim 23, wherein the means for moving includes an electromagnetic signal generator to provide an electromagnetic signal to move the at least one magnetically responsive member.

25. A bio-magnetic system as defined in claim 23, wherein the means for moving includes a magnet cooperatively disposed with the at least one magnetically responsive member such that the magnetic field of the magnet acts on the at least one magnetically responsive member to move the at least one magnetically responsive member to a desired position.

26. A bio-magnetic system as defined in claim 23, wherein the means for moving includes another at least one magnetically responsive member having an attachment mechanism for bonding with integrins of an epithelium of tissue in the human body such that the magnetically responsive members react to each other to move.

27. A bio-magnetic system as defined in claim 26, wherein the magnetically responsive members are magnetic with opposite magnetic polarities between the first-mentioned at least one magnetically responsive member and the another at least one magnetically responsive member.

28. A bio-magnetic system as defined in claim 26, wherein the magnetically responsive members are magnetic with the same magnetic polarity between the first-mentioned at least one magnetically responsive member and the another at least one magnetically responsive member.

29. A method for moving a constituent in a human body, comprising displacing with a magnetic field a magnetically responsive member connected by cellular connection proteins to a cytoskeleton of a cell of a constituent of a human body such that the connected magnetically responsive member and cell move, wherein the constituent is selected from the group consisting of a tympanic membrane, a middle-ear ossicle, a round window membrane, an oval window membrane, a larynx, an eyelid, and a sphincter.

30. A method as defined in claim 29, wherein displacing with a magnetic field includes generating the magnetic field electromagnetically.

31. A method as defined in claim 29, wherein displacing with a magnetic field includes electromagnetically generating a time-varying magnetic field.

32. A method as defined in claim 29, wherein displacing with a magnetic field includes generating a moving magnetic field by moving a static magnetic field relative to the magnetically responsive member.

33. A method as defined in claim 29, wherein the magnetic field is a stationary, static magnetic field.

34. A method as defined in claim 29, wherein the magnetically responsive member is connected by integrin bonds with the cell of the constituent of the human body.

* * * * *